US005760177A

United States Patent [19]
Iwanaga et al.

[11] Patent Number: 5,760,177
[45] Date of Patent: Jun. 2, 1998

[54] LIPOPOLYSACCHARIDE BINDING PROTEIN AND PROCESS FOR PRODUCING THE SAME

[75] Inventors: Sadaaki Iwanaga; Shunichiro Kawabata; Tetsu Saito, all of Fukuoka, Japan

[73] Assignee: Seikagaku Kogyo Kabushiki Kaisha, Tokyo, Japan

[21] Appl. No.: 393,058

[22] Filed: Feb. 23, 1995

Related U.S. Application Data99

[63] Continuation of PCT/JP93/01180 Aug. 24, 1993.

[30] Foreign Application Priority Data

Aug. 24, 1992 [JP] Japan .................................. 4-247289

[51] Int. Cl.$^6$ .......................... C07K 14/00; A61K 39/385
[52] U.S. Cl. ...................... 530/350; 530/389.5; 530/396; 530/402; 530/413; 530/416; 530/417; 530/427; 530/820; 424/193.1; 424/194.1; 424/520; 424/547
[58] Field of Search ..................... 530/350, 389.5, 530/396, 402, 413, 416, 417, 427, 820; 424/193.1, 194.1, 520, 547

[56] References Cited

U.S. PATENT DOCUMENTS

| | | | |
|---|---|---|---|
| 4,076,701 | 2/1978 | Burton et al. | 260/112 B |
| 4,490,549 | 12/1984 | Johnson | 549/396 |
| 5,068,314 | 11/1991 | Nakamura et al. | 530/317 |
| 5,091,511 | 2/1992 | Sone et al. | 530/351 |
| 5,328,836 | 7/1994 | Shima et al. | 435/69.4 |
| 5,416,194 | 5/1995 | Nakamura et al. | 530/344 |

FOREIGN PATENT DOCUMENTS

| | | |
|---|---|---|
| 0 519 728 A2 | 12/1992 | European Pat. Off. . |
| 0-588 477 A2 | 3/1994 | European Pat. Off. . |

OTHER PUBLICATIONS

Iwanaga et al, *Bacterial Endotoxin: Recognition and Effector Mechanism*, J. Levin et al., eds., Elsevier Science Publishers, pp. 185–192, 1993.
Nakamura et al, *Eur. J. Biochem.*, vol. 154, pp. 511–521, 1986.
Nakamura et al, *J. Biochem.*, vol. 99, pp. 847–857, 1986.
Ding et al, *Biochimica et Biophysica Acta*, vol. 1202, pp. 149–156, 1993.
Shigenaga et al, *J. Biochem.*, vol. 114, pp. 307–316, 1993.
Saito et al, *The Journal of Biological Chemistry*, vol. 270, No. 24, pp. 14493–14499, Jun. 16, 1995.
Katsumi Matsuzaki et al., "Interactions of an Antimicrobial Peptide. Tachyplesin I. with Lipid Membranes", *Biochimica et Biophysica Acta*, 1070:259–264 (1991).
Fuminori Tokunaga et al., "Lipopolysaccharide-Sensitive Serine-Protease Zymogen (Factor C) of Horseshoe Crab Hemocytes", *Eur. J. Biochem.*, 167:405–416 (1987).

Yoshiki Miura et al., "A Limulus Intracellular Coagulation Inhibitor with Characteristics of the Serpin Superfamily", *The Journal of Biological Chemistry*, 269, No. 1:542–547 (1994).
S. Iwanaga et al., "Intracellular LPS–Binding Proteins and Peptides Found in Limulus Hemocytes", Bacterial Endotoxin: Recognition and Effector Mechanisms, J. Levin, C.R. Alving, R.S. Munford, P.L. Stutz, eds., Elsevier Science Publishers B.V. (1993).
Takahito Jomori et al., "Function of the Lipopolysaccharide–Binding Protein of *Perplaneta americana* as an Opsonin", *FEBS Letters*, 296, No. 3:283–286 (1992).
Takanori Nakamura et al., "Interaction Between Lipopolysaccharide and Intracellular Serine Protease Zymogen, Factor C, from Horseshoe Crab (*Tachypleus tridentatus*) Hemocytes", *J. Biochem.*, 103:370–374 (1988).
Robert I. Roth et al., "Lipopolysaccharide–Binding Proteins of *Limulus amebocyte* Lysate", *Infection and Immunity*, 61, No. 3:1033–1039 (1993).
Conceicao A.S.A. Minetti et al., "Purification and Characterization of an Endotoxin–Binding Protein with Protease Inhibitory Activity from *Limulus amebocytes*", *The Journal of Biological Chemistry*, 266, No. 31:20773–20780 (1991).
Nam Gyu Park et al., "Conformation of Tachyplesin I from *Tachypleus tridentatus* When Interacting with Lipid Matrices", *Biochemistry*, 31:12241–12247 (1992).
Yoshiki Miura et al., "Preparation and Properties of Monoclonal Antibodies Against Lipopolysaccharide–Sensitive Serine Protease Zymogen, Factor C, from Horseshoe Crab (*Tachypleus tridentatus*) Hemocytes", *J. Biochem.*, 112:476–481 (1992).
Yoshiki Miura et al., "A Limulus Intracellular Coagulation Inhibitor Type 2", *The Journal of Biological Chemistry*, 270, No. 2:558–565 (1965).

*Primary Examiner*—Cecilia J. Tsang
*Assistant Examiner*—Abdel A-Mohamed
*Attorney, Agent, or Firm*—Testa, Hurwitz & Thibeault, LLP

[57] ABSTRACT

The invention provides a lipopolysaccharide (LPS) binding protein isolated from horseshoe crab. The LPS binding protein is isolated by (i) extracting the hemocyte membrane fraction of horseshoe crab with a polyethylene glycol ether type nonionic surface active agent in the presence of Ca ions, (ii) combining the extract with immobilized LPS under conditions that permit the LPS binding protein to bind the immobilized LPS to produce an LPS-LPS binding protein complex, and (iii) harvesting the LPS binding protein released from the complex in the presence of a chelating agent. The isolated LPS binding protein has a molecular weight of about 27,000 daltons as determined by SDS polyacrylamide gel electrophoresis and is operative to bind a lipopolysaccharide endotoxin. Accordingly, the isolated LPS binding protein can be used for detecting endotoxin and/or removing endotoxin from an injectable medicine.

11 Claims, 3 Drawing Sheets

LIPOPOLYSACCHARIDE BINDING PROTEIN AND PROCESS FOR PRODUCING THE SAME

This is a continuation-in-part of copending application International application PCT/JP01180 filed on Aug. 24, 1993 and which designated the U.S.

FIELD OF THE INVENTION

This invention relates to a novel lipopolysaccharide (hereinafter sometimes referred to simply as LPS) binding protein obtained from hemocyte membrane fraction of horseshoe crab and process for producing the same. More particularly, this invention relates to the LPS binding protein isolated from hemocyte membrane fraction of horseshoe crab with an affinity carrier immobilized with LPS.

The solid phase carrier which binds with the LPS binding protein of the present invention can be used as an agent for the adsorption and removal of endotoxin and a detection reagent of endotoxin by a sandwich method.

BACKGROUND OF THE INVENTION

Endotoxin is a lipopolysaccharide existing on the surface of the outer membrane of Gram negative bacteria and exhibits pyrogenicity, endotoxin shock, inlammation and Schwarzman reaction in mammals leading to tissue damage and multiple organ failure. Therefore, no contamination with endotoxin in injectable medicines which are directly administered in blood or cerebrospinal fluid is allowable and the removal of endotoxin is indispensable. Thus, the endotoxin test is compulsory for the production of medicines.

Heretofore, various endotoxin adsorptive and removal agents have been developed such as an immobilized polymyxin carrier (Japanese Patent Publication Nos. 16389 (1989) and 64153 (1991)), and carriers made of nylon or chitosan (Japanese Unexamined Patent Publication (Kokai) No. 109940 (1991)). However, these conventional carriers could not satisfy complete adsorption and removal of endotoxin. So-called sandwich determination methods of endotoxin by adsorption of endotoxin in a LPS binding protein or peptide immobilized on a carrier has been developed (Japanese Unexamined Patent Publication (Kokai) No. 222265 (1988) and Japanese Non-examination Patent Publication No. 500850 (1990)). However, these methods have not generally been used.

DISCLOSURE OF THE INVENTION

One object of the present invention is to provide a LPS binding material which is applicable for an endotoxin adsorptive and removal agent or a determination reagent. Another object of the present invention is to provide a process for the preparation of the above mentioned material from the blood of horseshoe crabs.

The inventors of the present invention found materials in horseshoe crab hemocyte treated products which bind with LPS and accomplished inventions of anti-lipopolysaccharide factor (hereinafter abbreviated as ALF) (Japanese Unexamined Patent Publication (Kokai) No. 13517 (1983)) and polypeptide factors (tachyplesin, polyphemusin) Japanese None-examination Patent Publication No. 500194 (1990), Japanese Unexamined Patent Publication (Kokai) Nos. 53799 and 152987 (1990)).

The inventors further investigated a LPS binding protein or peptide in the hemocytes of horseshoe crabs and found a novel LPS binding protein having quite different molecular weight and physiological activity from those of ALF, tachyplesin and polyphemusin, determined its primary structure and accomplished the present invention.

That is, the present invention relates to the LPS binding protein which is obtained by the steps of extracting a hemocyte membrane fraction of horseshoe crab with a polyethylene glycol ether type nonionic surface active agent in the present of $Ca^{2+}$, subjecting the extract to affinity chromatography using LPS as a ligand, and eluting with an eluent containing a chelating agent. The LPS binding protein thus obtained has the following physicochemical properties:

(i) shows a single band with SDS-polyacrylamide gel electrophoresis (SDS-PAGE) under reducing conditions, (ii) has a molecular weight of about 27,000 Daltons estimated from SDS-PAGE under reducing conditions, (iii) consists of 221 amino adds, and (iv) binds with LPS in the presence of $Ca^{2+}$and is dissociated from a complex with LPS in the presence of a chelating agent.

The LPS binding protein of the present invention preferable has a following primarily amino add structure:

| Val 1 | Gln | Trp | His | Gln 5 | Ile | Pro | Gly | Lys | Leu 10 | Met | His | Ile | Thr | Ala 15 |
|---|---|---|---|---|---|---|---|---|---|---|---|---|---|---|
| Thr | Pro | His | Phe | Leu 20 | Trp | Gly | Val | Asn | Ser 25 | Asn | Gln | Gln | Ile | Tyr 30 |
| Leu | Cys | Arg | Gln | Pro 35 | Cys | Tyr | Asp | Gly | Gln 40 | Trp | Thr | Gln | Ile | Ser 45 |
| Gly | Ser | Leu | Lys | Gln 50 | Val | Asp | Ala | Asp | Asp 55 | His | Glu | Val | Trp | Gly 60 |
| Val | Asn | Arg | Asn | Asp 65 | Asp | Ile | Tyr | Lys | Arg 70 | Pro | Val | Asp | Gly | Ser 75 |
| Gly | Ser | Trp | Val | Arg 80 | Val | Ser | Gly | Lys | Leu 85 | Lys | His | Val | Ser | Ala 90 |
| Ser | Gly | Tyr | Gly | Tyr 95 | Ile | Trp | Gly | Val | Asn 100 | Ser | Asn | Asp | Gln | Ile 105 |
| Tyr | Lys | Cys | Pro | Lys 110 | Pro | Cys | Asn | Gly | Ala 115 | Trp | Thr | Gln | Val | Asn 120 |
| Gly | Arg | Leu | Lys | Gln 125 | Ile | Asp | Gly | Gly | Gln 130 | Ser | Met | Val | Tyr | Gly 135 |
| Val | Asn | Ser | Ala | Asn 140 | Ala | Ile | Tyr | Arg | Arg 145 | Pro | Val | Asp | Gly | Ser 150 |
| Gly | Ser | Trp | Gln | Gln 155 | Ile | Ser | Gly | Ser | Leu 160 | Lys | His | Ile | Thr | Gly 165 |
| Ser | Gly | Leu | Ser | Glu | Val | Phe | Gly | Val | Asn | Ser | Asn | Asp | Gln | Ile |

-continued

| | | | | 170 | | | | 175 | | | | | 180 |
|---|---|---|---|---|---|---|---|---|---|---|---|---|---|
| Tyr | Arg | Cys | Thr | Lys | Pro | Cys | Ser | Gly | Gln | Trp | Ser | Leu | Ile | Asp |
| | | | | 185 | | | | 190 | | | | | | 195 |
| Gly | Arg | Leu | Lys | Gln | Cys | Asp | Ala | Thr | Gly | Asn | Thr | Ile | Val | Gly |
| | | | | 200 | | | | 205 | | | | | | 210 |
| Val | Asn | Ser | Val | Asp | Ile | Tyr | Arg | Ser | Gly | | | | |
| | | | | 215 | | | | 220 | | | | | |

Furthermore, the present invention relates to a process for producing LPS binding protein having molecular weight of about 27,000 estimated from SDS-PAGE under reducing conditons, which comprises extracting a hemocyte membrane fraction of horseshoe crab with a polyethylene glycol ether type nonionic surface active agent in the presence of an alkaline earth metal ion, subjecting the extract to affinity chromatography using a LPS as a ligand, and eluting with aneluent containing a chelating agent.

The raw material hemocytemembrane fraction of horseshoe crab used for the present invention includes extraction residues of hemocyte free from soluble components obtained from the blood of horseshoe crabs, for example, *Limulus polyphemus* available in U.S.A., *Tachypleus tridentatus* available in Japan and China, *Tachypleus gigas* available in Thailand and Malay Peninsula, and *Carcinoscorpius rotundicauda* available in Thailand and Malay Peninsula. Hemocyte (amebocyte) are separated from the blood of horseshoe crab, physically or chemically degraded, and the soluble fraction is thoroughly extracted and removed to give the desired hemocyte membrane fraction of horseshoe crab in the residue.

Practically, the separated hemocytes of horseshoe crab are homogenized in a suitable buffer such as 0.02M Tris-Hcl buffer containing 50 mM NaCl, pH 8.0, and centrifuged to extract and remove soluble components, and the resultant residue is used as the hemocyte membrane fraction of horseshoe crab. An extraction residue by-produced during the preparation of horseshoe crab hemocyte lysate used for the endotoxin assay, and known as a horseshoe crab test agent, can be used as the hemocyte membrane fraction of horseshoe crab, as described, for example, in *J. Biochem.*, 80, 1011–1021 (1976).

The resultant fraction of horseshoe crab hemocyte membrane is ① extracted with a polyethylene glycol ether type nonionic surface active agent in the presence of an alkaline earth metal ion; and ② the extract is applied to an affinity chromatography column using LPS as a ligand and eluted with an eluent containing a chelating agent to give a proteinacous fraction of LPS binding protein of the present invention.

The extraction process ① is generally carried out by homogenization in an aqueous solution such as an approximately neutral buffer containing an alkaline earth metal ion as a salt, e.g., a chloride salt, for example, 0.02M Tris-HCl buffer containing 10 mM $CaCl_2$, pH 7.5–7.7 using a cell destroying apparatus (e.g., Waring Blender™, Waring Products Corp., Div. of Dynamics Corp. of America). The resultant homogenate is mixed with a polyethylene glycol ether type nonionic surface active agent and thoroughly extracted with stirring under conditions such as not to cause denaturation of the protein, for example at a temperature between 0° C. to room temperature, preferably at 4° C., for several hours. Then, the extraction mixture is separated by a conventional method, such as centrifugation, to remove the non-soluble substance (such as degraded hemocyte membrane particles) and, if necessary, low molecular weight compounds are removed by dialysis against an approximately neutral buffer, for example, 0.02M Tris HCl buffer containing 10 mM $CaCl_2$ and 0.5M NaCl, pH 7.5–7.7 for the following process of affinity chromatography.

A preferred alkaline earth metal ion used in the process is calcium ion, $Ca^{2+}$, and its suitable concentration is about 10 mM for chloride, but the type and concentration can be determined empirically using no more than routine experimentation according to the types of alkaline earth metal ions and their salts. Polyethylene glycol ether type nonionic surface active agents such as polyethylene glycol alkyl ethers synthesized from ethylene oxide and higher alcohol are preferably used, particularly polyethylene glycol monododecyl ether having an alkyl group of 12 carbon atoms is preferred. Typical examples of these surface active agents include Lubrol™ PX (Imperial Chemical Ind.; Nacalai Tesque Inc.), Atlas™ G-2133 and G-3705 (Atlas Powder Co., Ltd.), allof which are known in the art under the respective generic and chemical names as Polidocanoland α-dodecy-ω-hydroxypoly (oxy-1,2-ethanediyl). The concentration of the surface active agent in the extract is not restrictive, but 0.1–10 w/w %, preferably 0.5–5 w/w %, is suitably used.

The affinity chromatography process ② is performed by contacting the extract obtained in the process ① on an affinity chromatography carrier using LPS as a ligand, which is preliminary equilibrated with the buffer used for the dialysis by a batch or a column method to specifically adsorb the LPS binding protein of the present invention. The contacted carrier is thoroughly washed with the buffer used for the dialysis, then eluted with an eluent containing a chelating agent while monitoring the concentration of the protein in the eluate to collect the LPS binding protein of the present invention.

The carrier of affinity chromatography using LPS as a ligand is prepared by contacting an LPS aqueous solution or suspension to a chromatography carrier for ligand immobilization having a suitable functional group for the immobilization of LPS to cause a coupling reaction. LPSs derived from various Gram negative bacteria can be used, but LPS derived *Escherichia coli* (hereinafter abbreviated as *E. coli*), preferably *E. coli* 0111:B4 is suitably used. Any chromatographic carrier used for the immobilization of ligand can be used without particular prerequisite, but epoxy activated agarose gel carrier, e.g., epoxy activated Sepharose™ 6B (Pharmacia Biosystems Inc.) is preferably used. Practically, the affinity chromatography carrier can be prepared by mixing of micelles, which is obtained by dispersion of LPS powder in a suitable buffer at about pH 11, e.g. 0.1M $Na_2CO_3$ buffer, and by ultrasonication with an activated type chromatography carrier for ligand immobilization, and separating of solid and liquid components.

As the eluting solution containing a chelating agent, a buffer at about neutral pH, for example 0.02M Tris-HCl buffer containing 0.1M NaCl, pH 7.5–7.7, containing a chelating agent may be used. As the chelating agent, usually, ethylenediaminetetraacetic acid (EDTA) is used, but other known chelating agents such as diamino-propanoltetraacetic acid (DPTA-OH), glycol ether diamine-tetraacetic acid (GEDTA) and diaminopropanetetraacetic acid can be used instead of EDTA. EDTA is suitably used at concentrations of about 25 mM.

The eluate obtained by the affinity chromatography process ② generally contains no protein other than the aimed product, but further conventional purification methods such as gel filtration, ion exchange chromatography, reverse phase chromatography and electrophoresis may be used to give further purified product.

Determination of protein content during the purification process can be carried out by measuring the UV absorption at a wave length of 280 nm.

The resultant LPS binding protein is subjected to a reverse phase HPLC to remove salts and a small amount of impurities to determine amino acid composition or amino acid sequence.

The LPS binding protein of the present invention is a novel LPS binding protein and has different molecular weight, amino acid sequence, and factor C activation from those of ALF, tachyplesin, polyphemusin, and lipopolysaccharide binding protein derived from rabbit neutrophils.

Further, the obtained protein can be immobilized with a suitable carrier as well as those conventional LPS binding proteins and can be used as an assay reagent for the detection of lipopolysaccharides (endotoxin) by sandwich method, and as agent for the adsorption and removal of endotoxin by effective adsorption and removal of endotoxin from water for injection, various medicines or body fluids such as blood. Furthermore, the protein is expected to be applicable for the treatment and prevention of Gram negative bacterial sepsis with its physiological properties. The protein of the present invention also is useful as an antibacterial, bactericidal or antiseptic agent against Gram negative bacteria. The forms, doses and routes of administration of pharmaceutical preparations of the agent are similar to those described in U.S. Pat. No. 5,242,902, the entire disclosure of which is hereby incorporated by reference.

THE BEST MODE FOR CARRYING OUT THE PRESENT INVENTION

The present invention will be explained by the following examples.

Example 1
[Preparation of LPS binding protein]

(1) Preparation of LPS immobilized carrier

In 5 ml of 0.1M $NaCO_3$ buffer, 5 mg of LPS powder (derived from *E. coli* 0111:B4, List Biological Laboratories Co., Ltd.) was dispersed and ultrasonicated at 45 kHz for about one minute to give a homogenous micelle dispersion. The dispersion was added to 3.34 g of an epoxy-activated Sepharose™ 6B (Pharmacia Biosystems Corp.) washed with distilled water and the same buffer, and made about 15 ml in total. The mixture was caused to react at 37° C. for 16 hours with stirring. After the reaction, the reaction mixture was filtered with a glass filter (G3), the resultant gel was washed with distilled water on the filter, suspended in a monoethanolamine solution to make 1M final concentration. The suspension was stirred at 37° .C overnight, filtered with a glass filter (G3) and the resultant gel was thoroughly washed with distilled water to give an LPS immobilized carrier.

(2) Preparation of hemocyte membrane function of horseshoe crab.

In 800 ml of 0.02M Tris-HCl buffer containing 50 mM NaCl, pH 8.0,155 g of hemocyte of Tachypleus tridentatus was added and homogenized for 3 minutes with a high speed homogenizer (Hiscotron™, Nippon Seimitsu Kogyo Co., Ltd.). The homogenate was centrifuged at 8,000 rpm for 30 minutes. The precipitates were washed with 400 ml of the same buffer, homogenized and centrifuged by similar manners shown above to give similar precipitates. The washing procedure was repeated further twice to thoroughly extract the soluble fraction in the hemocyte and to give 250 g of the residue.

(3) Preparation of LPS binding protein

In 950 ml of 0.02M Tris-HCl buffer containing 10 mM of $CaCl_2$, pH 7.5, 250 g of the residue was added and homogenized with a Waring Blender™. Then 50 ml of 10 w/w % of Lubrol™ was added to the homogenized mixture and stirred for 3 hours at 4° C. The insoluble portions were removed by centrifugation at 8,000 rpm for 30 minutes and the soluble fraction was dialyzed against to 0.02M Tris-HCl buffer containing 10 mM $CaCl_2$ and 0.5M NaCl, pH 7.5.

Figure 1:
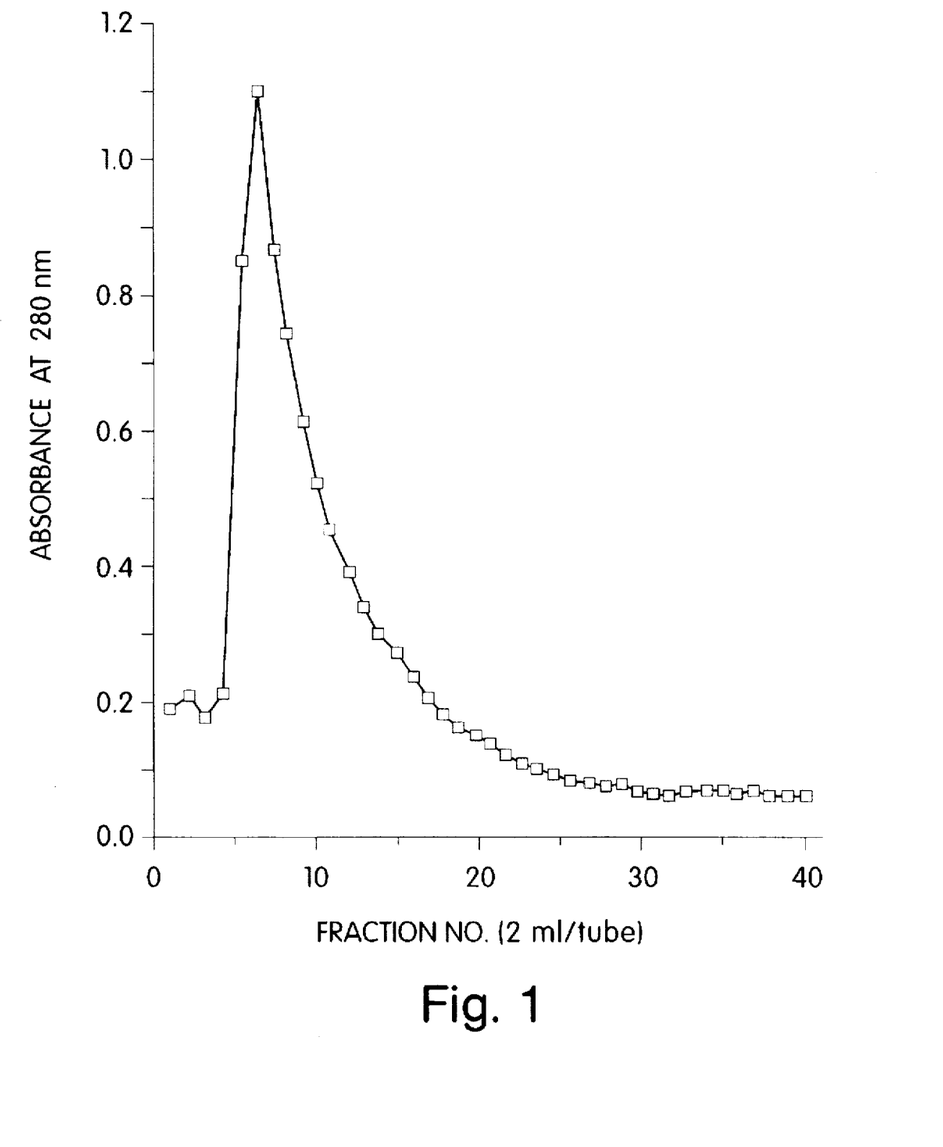
FIG. 1 shows the elution profile of the protein of the present invention from the column according to Example 1.
Figure 2:
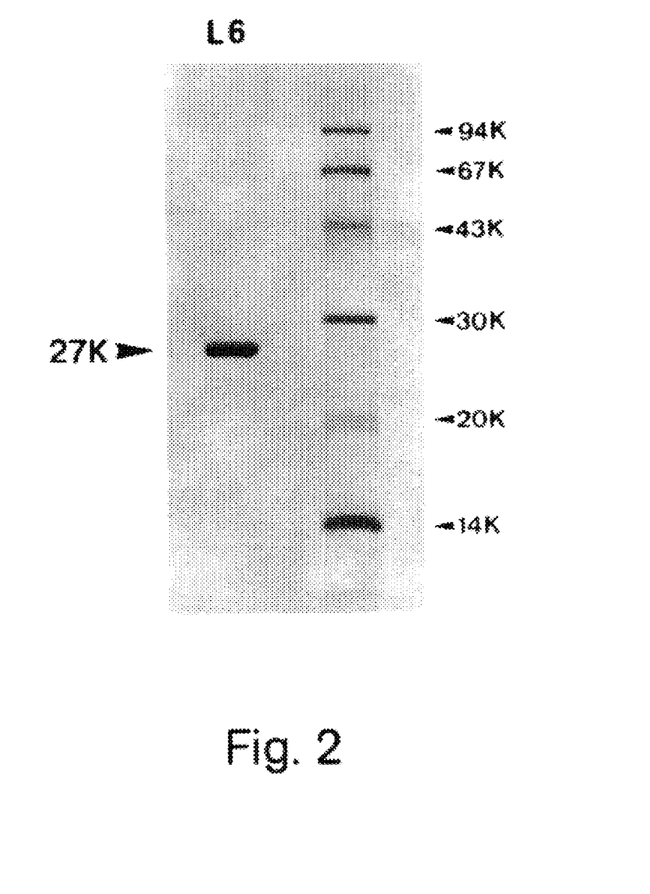
FIG. 2 shows the SDS-PAGE pattern of the protein of the present invention under reducing conditions according to Example 1. The right pattern shows the protein of the present invention and the left pattern shows a marker. The numerals indicate the molecular weight (unit: $10^3$ dalton). LMW, Kit E (Pharmacia Biosystems Corp.) was used as a marker.

The retentate dialysate was mixed with the LPS immobilized carrier equilibrated with the aforementioned buffer for dialysis (see aforementioned (1)) and packed in a column. The packed column was thoroughly washed with the same buffer and the adsorbed protein was eluted with 0.02M Tris-HCl buffer containing 0.1M NaCl and 25 mM EDTA, pH 7.5. The results are shown in FIG. 1. In the present example, fractions following 10 ml or over of the eluate were collected. The collected proteinacous fraction was purified into the final product of LPS binding protein. Finally, LPS binding protein exhibiting total UV absorption of about 9.0 at 280 nm was obtained from 155 g of hemocyte. The resultant protein showed a single band in SDS-PAGE under reducing conditions as shown in FIG. 2 and had molecular weight of about 27,000 daltons.

Figure 3:
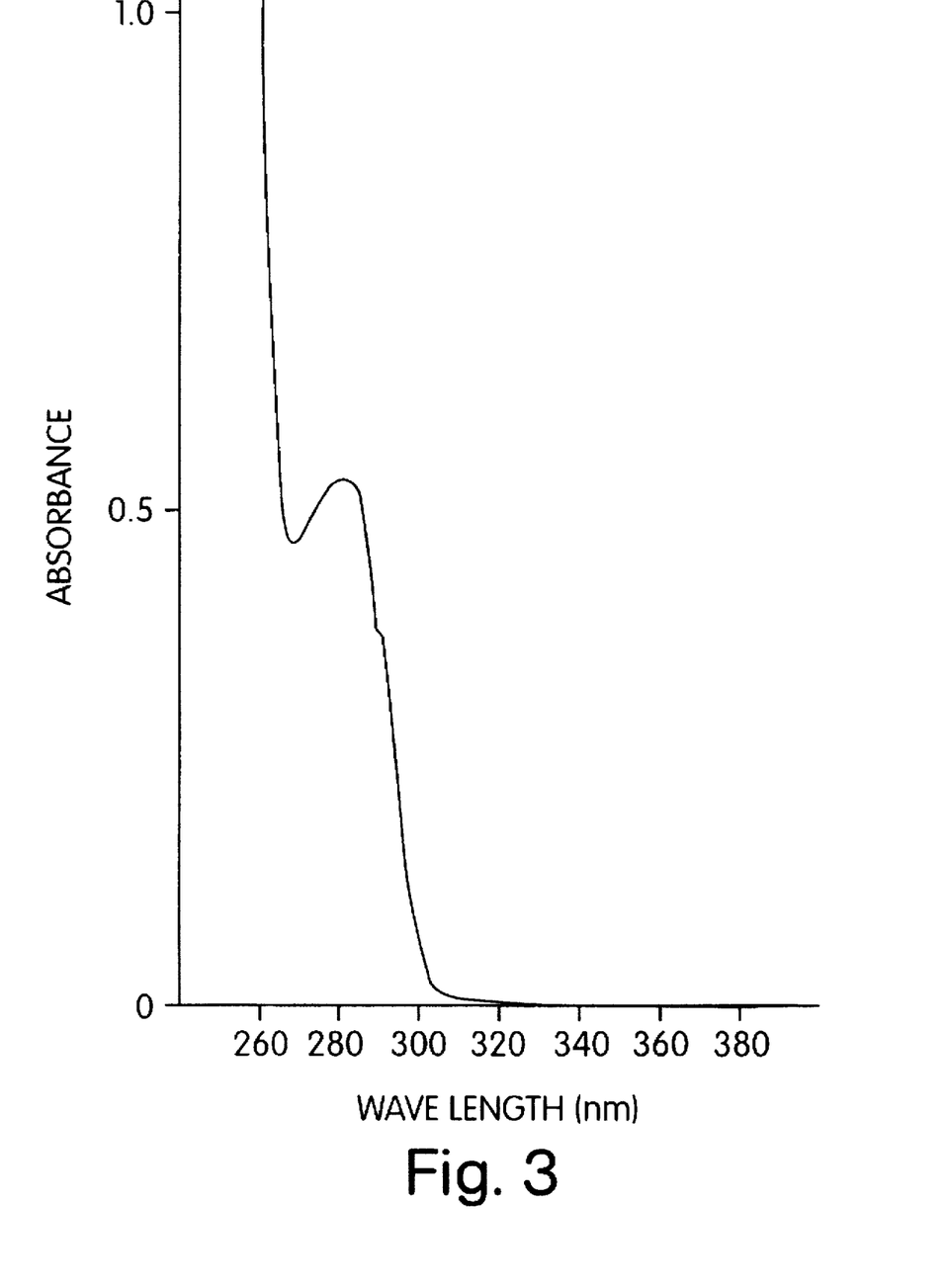
FIG. 3 shows the UV absorption spectrum of the protein of the present invention prepared by Example 1.

The UV absorption spectrum of the resultant protein is shown in FIG. 3.

Example 2
[Amino acid analysis and determination of amino acid sequence of the protein]

The purified LPS binding protein obtain by Example 1 was applied to $TSK_{gel}^{RTM}$ Phenyl-5PW RP (4.6×75 mm) (TOSOH Corp.) equilibrated with 0.1 v/v% $CF_3COOH$ and the column was thoroughly washed. The adsorbed protein was eluted using a linear gradient elution with $CH_3CN$ at concentrations of 8 v/v % at 10 minutes, 16 v/v% at 15 minutes, 48 v/v % at 105 minutes and 80 v/v % at 110 minutes, and at a flow rate of 0.5 ml/min. The eluted protein was monitored with an UV absorption at 214 nm. The fractions exhibiting high concentration of the protein were collected.

The resultant LPS binding protein was hydrolyzed with 6M HCl for 24,48 and 72 hours or with 4M methanesulfonic acid and then the amino acid composition was determined. The results are shown in Table 1. As shown in the Table 1, 9 moles of tryptophan was found in one mole of the protein. Thus, the protein of the present invention is similar to lectin, which has high content of tryptophan. Thus, the protein of the present invention is presumed to recognize a particular sugar chain as well as lectin. The determined amino add composition by amino acid analysis consisted with that of theoretical amounts calculated from the amino acid sequence.

The amino acid sequence of the resultant LPS binding protein was determined by a vapor phase Edman degradation method (Model 477A, Applied Biosystems, Inc.) and the amino acid sequence shown in Sequence ID No. 1 was obtained.

The protein of the present invention forms a complex with LPS (endotoxin) in the presence of $Ca^{2+}$ but, the protein is dissociated from the complex in the presence of a chelating agent such as EDTA.

Endotoxin activates factor C which participates in the coagulation of body fluid of horseshoe crab, and ALF and tachyplesin inhibit the factor C activation by endotoxin. However, the protein of the present invention has no such activity.

TABLE 1

| Amino Acid | Found[a] (No. of residue/molecule) | Calculated (No. of residue/molecule) |
|---|---|---|
| Asp | 29.0 | 14 |
| Asn | — | 15 |
| Thr | 8.0 | 8 |
| Ser | 21.8 | 22 |
| Glu | 18.8 | 2 |
| Gln | — | 17 |
| Pro | 9.0 | 8 |
| Gly | 27.7 | 27 |
| Ala | 7.4 | 7 |
| ½ Cys[b] | 7.4 | 7 |
| Val[c] | 18.0 | 18 |
| Met | 2.4 | 2 |
| Ile[c] | 14.4 | 15 |
| Leu | 10.1 | 10 |
| Tyr | 9.8 | 10 |
| Phe | 2.1 | 2 |
| Lys | 11.5 | 11 |
| His | 5.3 | 6 |

TABLE 1-continued

| Amino Acid | Found[a] (No. of residue/molecule) | Calculated (No. of residue/molecule) |
|---|---|---|
| Arg | 9.9 | 10 |
| Trp[d] | 8.0 | 9 |
| Total | 220.6 | 221 |

[a] The mean values after hydrolysis for 24, 48 and 72 hrs. The values of Ser and Thr were extrapolated to 0 hr.
[b] Determined as carboxymethylcysteine after modification by iodoacetamide.
[c] Obtained after 72 hrs. hydrolysis.
[d] Obtained by 4M methanesulfonic acid method.

Practically, no influence was found on the activation of factor C by mixing the protein of the present invention eluted from the LPS immobilized carrier with EDTA and endotoxin in the presence of $Ca^{2+}$.

Heretofore, LPS binding protein such as ALF or polyphemusin was isolated from *Limulus polyphemus* available in U.S.A., and ALF or tachyplesin was isojated from *Tachypleus tridentatus* available in Japan. Furthermore, many other LPS binding proteins have been reported. The properties of the LPS binding protein of the present invention were compared with those of known proteins and the results are shown in Table 2. Antibacterial activity of the proteins of the present invention were measured by the method described in *Infections and Immunity*, 42 10–14 (1983) using Gram-negative bacteria (*E. coli*).

The protein of the present invention exhibited antibacterial activity against the Gram-negative bacteria *E. coli*, as demonstrated above. Similar antibacterial activity against other Gram-negative bacteria is expected. The protein of the present invention is useful as an antibacterial, bactericidal or antiseptic agent against Gram-negative bacteria.

The protein of the present invention is different from conventional anti-lipopolysaccharide factor (ALF), tachyplesin and polyphemusin derived from horseshoe crab in molecular weight and numbers of amino acid residues. Furthermore, the protein of the present invention does not influence factor C activation by endotoxin though conventional anti-lipopolysaccharide factors (ALF) etc., inhibit or suppress factor C activation, or activate or stimulate the activity. Thus, the physiological activity of the protein of the present invention is far different from those of conventional anti-lipopolysaccharide factors. In addition, the protein of the present invention is different from a lipopolysaccharide binding protein and a basic anti-microbial protein produced by neutrophil which have comparatively similar properties. Thus, the protein of the present invention is a clearly different novel protein.

TABLE 2

| Substance (Name of species) | Molecular weight (No. of amino acid residue) | Antibacterial activity | LPS binding activity | Activity to factor C[a] | Reference |
|---|---|---|---|---|---|
| Protein of the present invention *Taphypleus tridentatus* | 27,000 (221) | Gram − | Present[b] | No | — |
| Anti-lipopolysaccharide factor (ALF) *Tachypleus tridentatus* | 11,600 (102) | Gram − | Present | Inhibition | J. Biol. Chem. 261, 7357 (1986) |
| Anti-lipopolysaccharide factor (ALF) *Limulus polyphemus* | 11,800 (101) | Gram − | Present | Inhibition | J. Biochem. 101, 1321 (1987) |
| Tachyplesin *Tachypleus Tridentans* | 2,260 (17) | Gram +, − Fungi | Present | Inhibition | Japanese None-examination Patent Publication No. 500194 (1990) |
| Polyphemusin *Limulus polyphemus* | 2,450 (18) | Gram +, − Fungi | Present | Inhibition | J. Biochem., 106, 633 (1988) |

TABLE 2-continued

| Substance (Name of species) | Molecular weight (No. of amino acid residue) | Antibacterial activity | LPS binding activity | Activity to factor C[a] | Reference |
|---|---|---|---|---|---|
| Lipopolysaccharide binding protein (Rabbit neutrophil) | 60,000 | Gram − | Present | Unknown | J. Biol. Chem., 263, 13479 (1988) |
| Basic anti-microbial protein (Neotrophil) | 37,000 and 57,000 | Positive | Unkown | Unknown | Infect. Immun., 53, 651 (1986) |

[a] Influence to factor C activation with LPS.
[b] Binding with LPS immobilized carrier.

Industrial applicability

The novel protein of the present invention bound with lipopolysaccharide and is useful as an endotoxin detecting agent and a treatment agent for the adsorption and removal of endotoxin from injectable medicines.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 221 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Val Gln Trp His Gln Ile Pro Gly Lys Leu Met His Ile Thr Ala Thr
  1               5                  10                  15

Pro His Phe Leu Trp Gly Val Asn Ser Asn Gln Gln Ile Tyr Leu Cys
             20                  25                  30

Arg Gln Pro Cys Tyr Asp Gly Gln Trp Thr Gln Ile Ser Gly Ser Leu
         35                  40                  45

Lys Gln Val Asp Ala Asp His Glu Val Trp Gly Val Asn Arg Asn
     50                  55                  60

Asp Asp Ile Tyr Lys Arg Pro Val Asp Gly Ser Gly Ser Trp Val Arg
 65                  70                  75                  80

Val Ser Gly Lys Leu Lys His Val Ser Ala Ser Gly Tyr Gly Tyr Ile
                 85                  90                  95

Trp Gly Val Asn Ser Asn Asp Gln Ile Tyr Lys Cys Pro Lys Pro Cys
                100                 105                 110

Asn Gly Ala Trp Thr Gln Val Asn Gly Arg Leu Lys Gln Ile Asp Gly
            115                 120                 125

Gly Gln Ser Met Val Tyr Gly Val Asn Ser Ala Asn Ala Ile Tyr Arg
    130                 135                 140

Arg Pro Val Asp Gly Ser Gly Ser Trp Gln Gln Ile Ser Gly Ser Leu
145                 150                 155                 160

Lys His Ile Thr Gly Ser Gly Leu Ser Glu Val Phe Gly Val Asn Ser
                165                 170                 175

Asn Asp Gln Ile Tyr Arg Cys Thr Lys Pro Cys Ser Gly Gln Trp Ser
            180                 185                 190
```

| Leu | Ile | Asp<br>195 | Gly | Arg | Leu | Lys | Gln<br>200 | Cys | Asp | Ala | Thr | Gly<br>205 | Asn | Thr | Ile |
| Val | Gly<br>210 | Val | Asn | Ser | Val | Asp<br>215 | Asn | Ile | Tyr | Arg | Ser<br>220 | Gly | | | |

We claim:

1. An isolated lipopolysaccharide binding protein comprising one or more of the following characteristics:
   (i) a molecular weight of about 27,000 daltons as estimated by SDS-polyacrylamide gel electrophoresis under reducing conditions;
   (ii) a polypeptide chain comprising about 221 amino acids; and
   (iii) is operative to bind lipopolysaccharide in the presence of $Ca^{2+}$ to produce a lipopolysaccharide-lipopolysaccharide binding protein complex, wherein said complex dissociates in the presence of a chelating agent.

2. The isolated lipopolysaccharide binding protein of claim 1, wherein said protein is further characterized as having antibacterial activity against Gram negative bacteria.

3. The isolated lipopolysaccharide binding protein of claim 2, wherein said Gram negative bacteria is *E. coli*.

4. The isolated lipopolysaccharide binding protein of claim 1, wherein said protein is further characterized as being operative to bind a lipopolysaccharide endotoxin that activates factor C without affecting the endotoxin activation of factor C.

5. A method for removing a lipopolysaccharide endotoxin from a sample, the method comprising the steps of:
   (a) combining the sample with the isolated lipopolysaccharide binding protein of claim 1 under conditions to permit the lipopolysaccharide binding protein to bind the endotoxin thereby to produce a lipopolysaccharide binding protein-endotoxin complex; and
   (b) separating the complex from the sample thereby to deplete the sample of the endotoxin.

6. An isolated lipololysaccharide binding protein comprising the amino acid sequence set fourth in Sequence ID No. 1.

7. A method for removing a lipopolysaccharide endotoxin from a sample, the method comprising the steps of:
   (a) combining the sample with the isolated lipopolysaccharide binding protein of claim 6 under conditions to permit the lipopolysaccharide binding protein to bind the endotoxin thereby to produce a lipopolysaccharide binding protein-endotoxin complex; and
   (b) separating the complex from the sample thereby to deplete the sample of the endotoxin.

8. A method for isolating a lipoplysaccharide binding protein having a molecular weight of about 27,000 daltons as determined by SDS-PAGE under reducing conditions, the method comprising the steps of:
   (a) extracting a hemocyte membrane fraction of horseshoe crab with a non-ionic surface active agent in the presence of an alkaline earth metal ion,
   (b) subjecting the extract to affinity chromatography using lipopolysaccharide as a ligand, and
   (c) eluting the lipopolysaccharide binding protein with an eluent containing a chelating agent.

9. The method of claim 8, wherein the alkaline earth metal ion is $Ca^{2+}$.

10. The method of claim 8, wherein the non-ionic surface active agent is a polyethylene glycol ethyer type non-ionic surface active agent.

11. The method of claim 10, wherein the polyethylene glycol ether type non-ionic surface active agent is polidocanol.

* * * * *

UNITED STATES PATENT AND TRADEMARK OFFICE
CERTIFICATE OF CORRECTION

PATENT NO. : 5,760,177
DATED : June 2, 1998
INVENTOR(S) : Iwanga et al.

It is certified that error appears in the above-identified patent and that said Letters Patent is hereby corrected as shown below:

In claim 1, column 11, line 11, delete the phrase "one or more of".

In claim 10, column 12, line 35, delete the word "ethyer" and replace with --ether--.

Signed and Sealed this

Twenty-fourth Day of November, 1998

*Attest:*

BRUCE LEHMAN

*Attesting Officer*  *Commissioner of Patents and Trademarks*